(12) United States Patent
Staggs et al.

(10) Patent No.: US 9,685,200 B2
(45) Date of Patent: Jun. 20, 2017

(54) APPARATUS, SYSTEM AND METHOD FOR CONSOLIDATING AND RECORDING HIGH DEFINITION SURGICAL VIDEO WITH A SURGICAL DATA OVERLAY

(71) Applicant: Abbott Medical Optics Inc., Santa Ana, CA (US)

(72) Inventors: James W. Staggs, Laguna Niguel, CA (US); Mark E. Steen, Santa Ana, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 90 days.

(21) Appl. No.: 14/485,218

(22) Filed: Sep. 12, 2014

(65) Prior Publication Data

US 2015/0131963 A1 May 14, 2015

Related U.S. Application Data

(60) Provisional application No. 61/877,762, filed on Sep. 13, 2013.

(51) Int. Cl.
| | |
|---|---|
| *H04N 5/89* | (2006.01) |
| *H04N 5/77* | (2006.01) |
| *H04N 9/80* | (2006.01) |
| *H04N 5/92* | (2006.01) |
| *G11B 31/00* | (2006.01) |
| *G11B 27/034* | (2006.01) |
| *H04N 5/04* | (2006.01) |
| *H04N 5/91* | (2006.01) |
| *H04N 7/18* | (2006.01) |
| *H04N 7/00* | (2011.01) |
| *H04N 11/00* | (2006.01) |

(Continued)

(52) U.S. Cl.
CPC ......... *G11B 31/006* (2013.01); *G11B 27/034* (2013.01); *H04N 5/04* (2013.01); *H04N 5/772* (2013.01); *H04N 5/91* (2013.01); *A61B 2090/3612* (2016.02); *H04N 5/76* (2013.01); *H04N 5/775* (2013.01); *H04N 9/8205* (2013.01)

(58) Field of Classification Search
USPC .......... 386/335, 224, 239, 248, 326; 348/61, 348/552, 565
See application file for complete search history.

(56) References Cited

U.S. PATENT DOCUMENTS 5,911,036 A 6/1999 Wright et al.
6,238,344 B1 * 5/2001 Gamelsky ................ A61B 8/00
128/903

(Continued)

OTHER PUBLICATIONS

International Search Report and Written Opinion for Application No. PCT/US2014/055455, mailed on Dec. 4, 2014, 12 pages.

*Primary Examiner* — Daquan Zhao
(74) *Attorney, Agent, or Firm* — Abbott Medical Optics Inc.

(57) ABSTRACT

An apparatus, system and method of consolidation of HD video and a surgical data overlay, such as for recordation in a single consolidated video capture recording of the HD video and surgical data overlay for subsequent playback and/or storage; and an apparatus, system and method for recording HD surgical video consolidated with a surgical data overlay in which an automated switch occurs between at least two surgical HD video sources based, at least in part, on then-active surgical aspects.

10 Claims, 3 Drawing Sheets

(51) Int. Cl.
*H04N 5/45* (2011.01)
*H04N 5/76* (2006.01)
*H04N 5/775* (2006.01)
*H04N 9/82* (2006.01)
*A61B 90/00* (2016.01)

(56) References Cited

U.S. PATENT DOCUMENTS

| 6,602,185 B1 | 8/2003 | Uchikubo |
| 2003/0159141 A1* | 8/2003 | Zacharias .............. A61B 19/52 725/37 |
| 2009/0040366 A1* | 2/2009 | Voelker ................. A61B 19/52 348/370 |

* cited by examiner

APPARATUS, SYSTEM AND METHOD FOR CONSOLIDATING AND RECORDING HIGH DEFINITION SURGICAL VIDEO WITH A SURGICAL DATA OVERLAY

CROSS-REFERENCES TO RELATED APPLICATIONS

This application claims priority to U.S. provisional application No. 61/877,762 filed on Sep. 13, 2013, the entire contents of which are incorporated herein by reference.

BACKGROUND OF THE INVENTION

Field of the Invention

The invention includes surgical video and data recoding techniques, and, more particularly, includes an apparatus, system and method for synchronizing and recording high definition surgical video and a surgical data overlay.

Description of the Background

High-definition video is understood to be video of a higher resolution than standard definition. High-definition is generally deemed to be any video image with more than 480 horizontal lines in North America, and a minimum of 720 scan lines. Further, images of standard resolution captured at very high rates by a high speed camera, such as greater than 60 frames/second, may also be considered high-definition.

High definition video may be provided via a Digital Visual Interface (DVI), which is a video display interface developed by the Digital Display Working Group (DDWG). The DVI may be used to connect a HD video source to a display device, such as a computer monitor. DVI was developed as an industry standard for the transfer of digital video content. The DVI is suitable to transmit uncompressed digital video, and can support multiple modes such as DVI-D (digital only), DVI-A (analog only), or DVI-I (digital and analog).

HDMI (High-Definition Multimedia Interface) is a compact audio/video interface suitable for transferring uncompressed video data and compressed/uncompressed digital data from a HDMI source device to a compatible computer monitor, video projector, digital television, or digital output device. HDMI replaces existing analog video standards.

The use of high definition microscopes for surgical embodiments, including in surgical and for post-surgical teaching embodiments, is on the rise correspondent with improvements in, proliferation of, and ease of use of, HD equipment. Further, it is well-known to monitor surgical data during a surgical event, and further to display and/or record the data digitally for teaching and learning purposes with regard to surgeries.

However, it is generally not presently the case that surgical data, such as may be accumulated or acted upon during a phacoemulsification surgery, is superimposed via an overlay on high definition video for recording for post-surgical use. Rather, the present state of the art is in its infancy with regard to providing surgical data overlays during use of high definition surgical video, and because the present state of the art does not allow for the recording of the high definition video, the present state of the art does not allow for the overlaid surgical data to be consolidated with, and recorded with, the high definition video.

Correspondingly, the present state of the art also does not provide a high definition recorder capable of recording with an overlay and using two automatically-alternated video data feeds. In rare instances in which a high definition recorder is provided in conjunction with a surgical environment, it is typically an external recorder based in a secondary computing system, and such a recording system typically requires a sophisticated and complex user interface, including requiring a manual selection as between various data feeds and synchronization. The need for this type of manual selection through a cumbersome interface is inefficient and unacceptable in operating room embodiments.

Therefore, the need exists for an apparatus, system and method of consolidation of HD video and a surgical data overlay, such as for recordation in a single consolidated video capture recording of the HD video and surgical data overlay for subsequent playback and/or storage. A need also exists for an apparatus, system and method for recording HD surgical video consolidated with a surgical data overlay in which an automated switch occurs between at least two surgical HD video sources based, at least in part, on then-active surgical aspects.

SUMMARY OF THE INVENTION

The present invention includes at least apparatuses, systems and methods for capturing a high definition (HD) video and a surgical data overlay in a single consolidated video capture. The apparatus, system and method may include a display overlay generator suitable to overlay surgical data relating to a surgical event onto the HD video, wherein the overlay is synchronized with the HD video of the surgical event; a HD digital video capture device suitable to capture the HD video and the overlay in the consolidated video capture in real-time during a surgical event; and a recorder suitable to record the consolidated video capture to at least one mass storage device.

The present invention additionally includes at least apparatuses, systems and methods for alternating between high definition (HD) video outputs, wherein each of the HD video outputs includes a surgical data overlay, during a surgical event. Such an apparatus, system or method may include at least a display overlay generator suitable to overlay surgical data relating to the surgical event onto a respective one of the HD video outputs, wherein the overlay is synchronized with the respective HD video output into a consolidated video output, and a computer processor-driven switch that switches at least a display of the consolidated video output correspondent to a first of the HD video outputs to a second consolidated video output correspondent to a second of the HD video outputs in accordance with a change from a first overlaid surgical data to a second overlaid surgical data.

Thus, the present invention provides at least an apparatus, system and method of consolidation of HD video and a surgical data overlay, such as for recordation in a single consolidated video capture recording of the HD video and surgical data overlay for subsequent playback and/or storage; and an apparatus, system and method for recording HD surgical video consolidated with a surgical data overlay in which an automated switch occurs between at least two surgical HD video sources based, at least in part, on then-active surgical aspects.

BRIEF DESCRIPTION OF THE FIGURES

Understanding of the present invention will be facilitated by consideration of the following detailed description of the preferred embodiments of the present invention taken in conjunction with the accompanying drawings, in which like numerals refer to like parts.

DETAILED DESCRIPTION

It is to be understood that the figures and descriptions of the present invention have been simplified to illustrate elements that are relevant for a clear understanding of the present invention, while eliminating, for the purpose of clarity, many other elements found in similar systems, apparatuses, and methods. Those of ordinary skill in the art may thus recognize that other elements and/or steps are desirable and/or required in implementing the present invention. However, because such elements and steps are well-known in the art, and because they do not facilitate a better understanding of the present invention, a discussion of such elements and steps is not provided herein. The disclosure herein is directed to all such variations and modifications to such elements and methods known to those skilled in the art.

Figure 1:
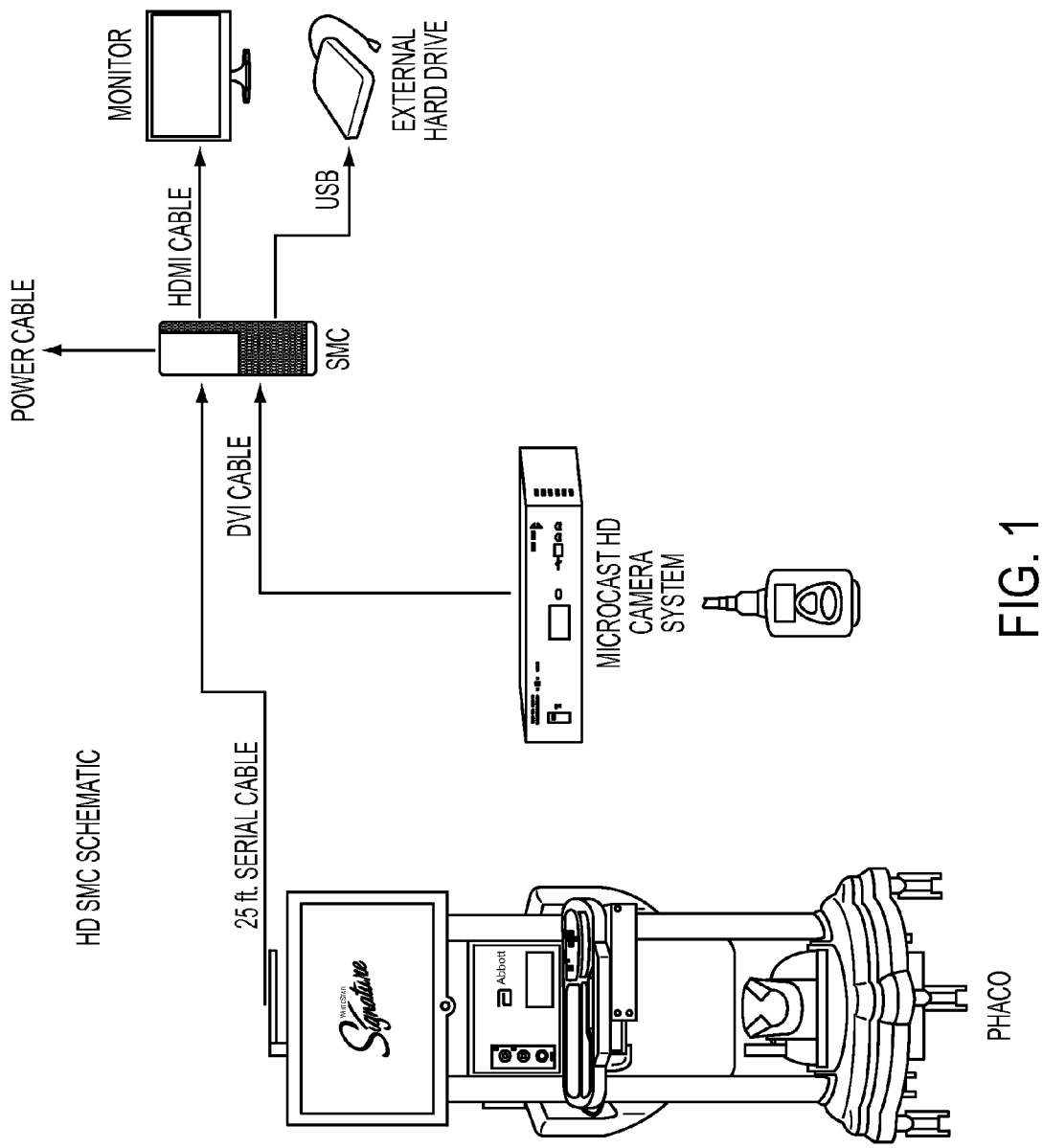
FIG. 1 illustrates an aspect of the instant invention.

As is illustrated in FIG. 1, embodiments of the present invention may be based on a computing system equipped with a DVI/HDMI digital video capture device. The video capture device is suitable to capture high definition video in real-time during a surgical event. In a particularly preferred embodiment, the capture device consolidates such that only the single device is required to capture high definition video, in real-time, with an inclusion of a video overlay of surgical data information superimposed on the recorded video output. Further, the consolidated video capture may be recorded to a mass storage device, such as a USB flash drive, hard drive, or the like.

As illustrated in FIG. 1, the currently disclosed embodiments may be included as an aspect of a surgical media center (SMC), such as is currently provided by Abbott Medical Optics Inc. (AMO). In embodiments, the SMC may include at least one computer processor and one or more computing memories for executing a software application capable of receiving the aforementioned real-time high definition video and the serial data from a surgical system, or, more particularly, from a phacoemulsification system, such as the WHITESTAR Signature phacoemulsification system provided by AMO. In such an embodiment, the high definition video data and serial surgical data may be combined and/or synchronized, such that a single real-time video is created that is suitable for output to a high definition monitor and/or for storage on the mass storage device.

Moreover, the SMC may include various other aspects in order to provide the ease of use of the present invention. For example, such aspects may include a remote control and/or simple user interfaces, such as may be provided on the phacoemulsification system, that may be used to start and/or stop a high definition consolidated video recording. Further, the simple user interface may be used to instruct, such as upon completion of a recording process, that the combined digital video file be transferred to storage, such as the aforementioned mass storage device. The simplicity of use of the instant invention makes for practical use thereof in an operating room setting.

In addition to the particular components disclosed herein, any commercially available hardware may be employed in a system such as that shown in FIG. 1. Further, those skilled in the art will appreciate that other types of video may be used in the instant invention, either as input or as output, and such other video types may be scaled, such to approximate high definition. For example, an extended definition camera output may be provided, wherein the extended definition camera output may be converted, such as by scaling, to a high definition format for synchronization with the surgical data overlay and for output of the combined video.

It will be further appreciated that any type of video acquisition device, computer, processor, or computing system may be employed in the present invention. Further, the use of the present invention in a phacoemulsification system is provided by way of example only. The present invention may be employed as a stand-alone video recorder for other surgical systems, including other ophthalmic surgical systems, such as femtosecond laser systems, laser cataract systems (LCS), Lasik systems, etc.

Figure 2:
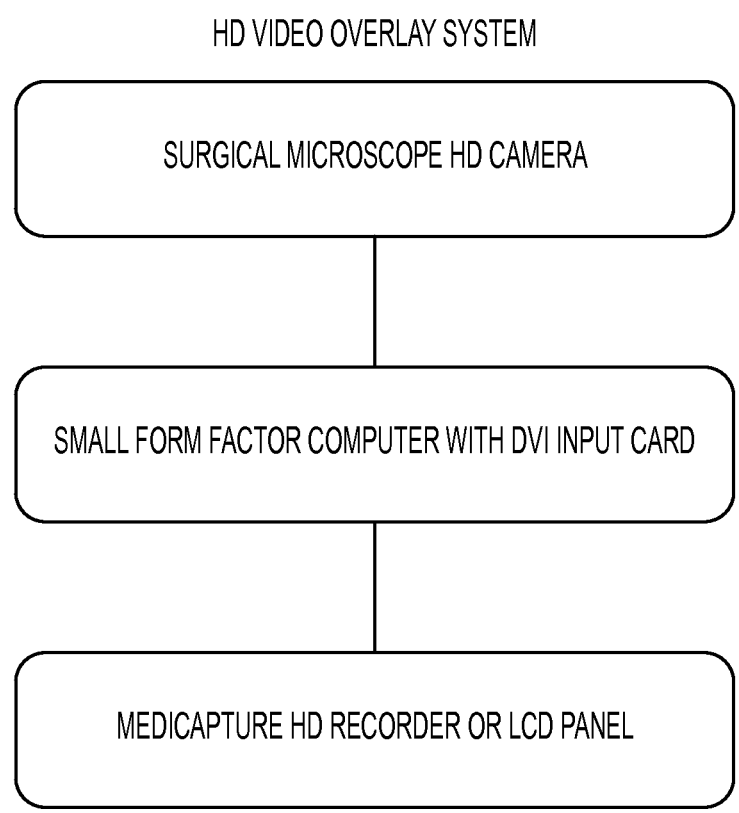
FIG. 2 illustrates an aspect of the instant invention.

FIG. 2 illustrates a flow diagram in accordance with the present invention. In the illustrated flow, and also in view of the exemplary embodiment of FIG. 1, a surgical microscope high definition camera may capture aspects of a surgical event. A computing system, such as a small form factor computing system with a DVI input, may receive the high definition camera feed, and may additionally receive serial data regarding the surgical event and synchronize with the high definition video. For example, surgical data is typically displayed on a surgical panel, such as the surgical panel provided with the WHITESTAR Signature system provided by AMO, and may be received and overlaid on the high definition video of the surgical event. Accordingly, such as through the use of a Medicapture high definition recorder or an LCD panel, a combined video may be obtained using the high definition camera input and the serial surgical data.

Figure 3:
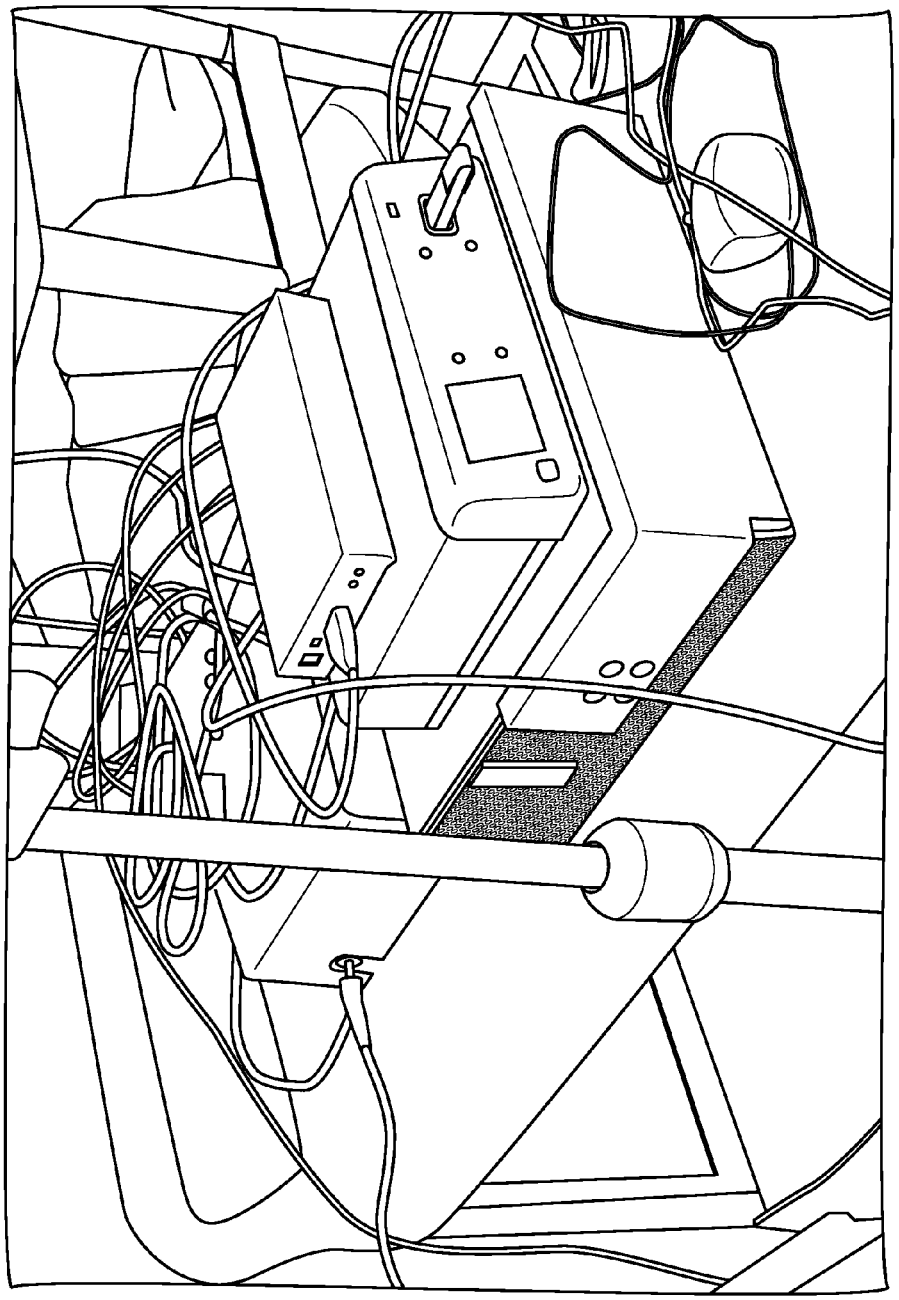
FIG. 3 illustrates an aspect of the instant invention.

FIG. 3 is an illustration of a physical high definition overlay system with a Medicapture HD recorder and an HD video scaler. As referenced above, those skilled in the art will appreciate that physical devices other than those illustrated in FIG. 3 may be employed in the present invention.

In aspects of the present invention, and as referenced above, a SMC in accordance with the present invention may automatically sense and/or select the signals from at least two different high definition sources based on the information sent by a surgical data generating instrument and during a particular point of a procedure. For example, switching between a phacoemulsification scope camera and a LCS femtocamera may occur during recording of the combined video discussed herein, such as based on the surgical data in the active overlay generated at a particular point of a surgical procedure. This is in stark contrast to the available art, in which an operator would typically manually switch between source videos, such as via an "AB" switch.

In the instant invention, automated switching of various available input videos may occur. For example, in a first step, the camera that is providing the active source may be assessed. In a second step, the surgical medical center may record and combine a data overlay that corresponds to the data generated according to the active camera. In a third step, recording may be stopped, and may become active for a different camera when a next part of a surgical procedure becomes active and the surgical overlay data generated corresponds to that next camera.

Although the invention has been described and pictured in an exemplary form with a certain degree of particularity, it is understood that the present disclosure of the exemplary form has been made by way of example, and that numerous changes in the details of construction and combination and arrangement of parts and steps may be made without departing from the spirit and scope of the invention as set forth in the claims hereinafter.

The invention claimed is:

1. A system, comprising:
a display overlay generator suitable to overlay surgical data relating to a surgical event onto a high definition (HD) video of the surgical event, wherein the overlay is synchronized with the HD video of the surgical event;
an HD digital video capture device suitable to capture the HD video and the overlay in a consolidated video capture in real-time during the surgical event; and
a recorder suitable to record the consolidated video capture to at least one mass storage device,
wherein the system is configured to select a signal for the HD video from among a plurality of video inputs based on at least some of the overlay surgical data relating to the surgical event.

2. The system of claim 1, wherein the HD digital video capture device is a DVI device.

3. The system of claim 1, wherein the HD digital video capture device is a HDMI device.

4. The system of claim 1, wherein the HD digital video capture device comprises a single device.

5. The system of claim 1, wherein the mass storage device comprises at least one of a USB flash drive and a hard drive.

6. The system of claim 1, wherein the surgical data comprises serial data.

7. The system of claim 1, wherein the surgical event is from a phacoemulsification system.

8. A system for alternating between at least a first high definition (HD) video output and a second HD video output, wherein the system automatically senses and selects a signal from at least a first video input and a second video input based on information sent by a surgical data generating system, the first video input and the second video input corresponding to the first HD video output and the second HD video output, respectively, and the first HD video output and the second HD video output include a surgical data overlay, during a surgical event, comprising:
a display overlay generator suitable to overlay surgical data relating to the surgical event onto at least the first HD video output and the second HD video output, wherein the overlay corresponding to the first HD video output is synchronized into a first consolidated video output and the overlay corresponding to the second HD video output is synchronized into a second consolidated video output;
a computer processor-driven switch that switches at least a display of the first consolidated video output correspondent to the first HD video output to a second consolidated video output correspondent to the second HD video output in accordance with a change from a first overlaid surgical data to a second overlaid surgical data.

9. The system of claim 8, wherein the change is indicative of a change in an active aspect of the surgical event.

10. The system of claim 9, wherein the surgical event is from a phacoemulsification system.

* * * * *